(12) United States Patent
Ito et al.

(10) Patent No.: US 11,937,040 B2
(45) Date of Patent: Mar. 19, 2024

(54) INFORMATION PROCESSING DEVICE, INFORMATION PROCESSING METHOD, AND STORAGE MEDIUM

(71) Applicant: NEC Corporation, Tokyo (JP)

(72) Inventors: Yoshitaka Ito, Tokyo (JP); Takayuki Arakawa, Tokyo (JP)

(73) Assignee: NEC CORPORATION, Tokyo (JP)

( * ) Notice: Subject to any disclaimer, the term of this patent is extended or adjusted under 35 U.S.C. 154(b) by 172 days.

(21) Appl. No.: 17/639,980

(22) PCT Filed: Sep. 12, 2019

(86) PCT No.: PCT/JP2019/035904
§ 371 (c)(1),
(2) Date: Mar. 3, 2022

(87) PCT Pub. No.: WO2021/048974
PCT Pub. Date: Mar. 18, 2021

(65) Prior Publication Data
US 2022/0295170 A1    Sep. 15, 2022

(51) Int. Cl.
*H04R 1/10* (2006.01)
*A61B 5/117* (2016.01)

(52) U.S. Cl.
CPC ............ *H04R 1/1041* (2013.01); *A61B 5/117* (2013.01)

(58) Field of Classification Search
CPC .............................. H04R 1/1041; A61B 5/117
USPC ............................ 381/1, 56, 58, 74, 98, 124
See application file for complete search history.

(56) References Cited

U.S. PATENT DOCUMENTS

| 2008/0262382 A1* | 10/2008 | Akkermans | G06V 40/10 600/559 |
| 2009/0087003 A1* | 4/2009 | Zurek | G06V 40/10 704/E15.001 |
| 2011/0295598 A1 | 12/2011 | Yang et al. | |
| 2013/0243226 A1 | 9/2013 | Tokoro et al. | |
| 2018/0307818 A1* | 10/2018 | Yano | A61B 5/117 |
| 2019/0012447 A1 | 1/2019 | Lesso | |

(Continued)

FOREIGN PATENT DOCUMENTS

| CN | 108803859 A | 11/2018 |
| JP | 2005-339265 A | 12/2005 |

(Continued)

OTHER PUBLICATIONS

EP Office Action for EP Application No. 19944898.6, dated Aug. 9, 2022.

(Continued)

*Primary Examiner* — William A Jerez Lora
(74) *Attorney, Agent, or Firm* — Sughrue Mion, PLLC

(57) ABSTRACT

Provided is an information processing device comprising an acquisition unit configured to acquire acoustic characteristics in a frequency domain based on a sound wave propagating in a head of a user and an extracting unit configured to generate a first frequency response function having a rational polynomial equation to extract feature quantity used for biometric authentication of the user based on the first frequency response function, the rational polynomial equation including terms indicating feature of a peak of the acoustic characteristics in a denominator and terms indicating feature of a notch of the acoustic characteristics in a numerator.

16 Claims, 12 Drawing Sheets

(56) References Cited

U.S. PATENT DOCUMENTS

| | | |
|---|---|---|
| 2019/0189129 A1 | 6/2019 | Arakawa et al. |
| 2019/0258789 A1 | 8/2019 | Koshinaka et al. |
| 2021/0103646 A1 | 4/2021 | Koshinaka et al. |

FOREIGN PATENT DOCUMENTS

| | | | |
|---|---|---|---|
| JP | 2008-217521 | A | 9/2008 |
| JP | 2009-509575 | A | 3/2009 |
| JP | 2010-086328 | A | 4/2010 |
| JP | 2013-528836 | A | 7/2013 |
| JP | 2013-219731 | A | 10/2013 |
| JP | 2016-161413 | A | 9/2016 |
| JP | 2017-085362 | A | 5/2017 |
| WO | 2006/074082 | A1 | 7/2006 |
| WO | 2014/061578 | A1 | 4/2014 |
| WO | 2018/034178 | A1 | 2/2018 |
| WO | 2018/051950 | A1 | 3/2018 |
| WO | 2018/101317 | A1 | 6/2018 |
| WO | 2018/198310 | A1 | 11/2018 |

OTHER PUBLICATIONS

Akkermans Ton H et al., "Acoustic Ear Recognition", (Jan. 5, 2006), SAT 2015 18th International Conference, Austin, TX, USA, Sep. 24-27, 2015, pp. 697-705.

Liu et al., "Earprint Transient Evoked Otoacoustic Emission for Biometrics", IEEE Transactions on Information Forensics and Security, IEEE, USA, vol. 9, No. 12, Dec. 1, 2014, pp. 2291-2301.

International Search Report for PCT Application No. PCT/JP2019/035904, dated Dec. 10, 2019.

CN Office Action for CN Application No. 201980100182.0, dated Aug. 18, 2023 with English Translation.

Baocheng Lin et al.,"Chinese Speaker Recognition Based on ARMA Model", Jun. 15, 1998, Acta Acustica, No. 3, pp. 229-234, China.

Qian Li et al., "Research On Nasal Cavity Parameters Of Speaker Recognition System", Jun. 30, 2012, Technical Acoustics, 03, pp. 61-65, China.

Xuesong Ye,"The study of the diagnosis of coronary artery disease based on neural networks and the heart 4 sound wavelet analysis", Feb. 28, 1999, Journal of Zhejiang University (Engineering Science) 02, pp. 15-20, China.

Zhijie Xu et al.,"Analysis Of Real And Complex Coefficient Matrices Using Least-Square Complex 5 Frequency Domain Method", Jun. 30, 2013, Noise and Vibration Control, 03, pp. 25-29, China.

\* cited by examiner

INFORMATION PROCESSING DEVICE, INFORMATION PROCESSING METHOD, AND STORAGE MEDIUM

This application is a National Stage Entry of PCT/JP2019/035904 filed on Sep. 12, 2019, the contents of all of which are incorporated herein by reference, in their entirety.

TECHNICAL FIELD

The disclosure relates to an information processing device, an information processing method, and a storage medium.

BACKGROUND ART

Patent Literature 1 discloses an earphone having a personal authentication function based on an acoustic signal propagating in a user's head. The personal authentication apparatus disclosed in Patent Literature 1 extracts a logarithmic spectrum, a mel-frequency cepstral coefficient, a linear predictive analysis coefficient, and the like as feature quantities from acoustic characteristics to use the feature quantities for user authentication.

CITATION LIST

Patent Literature

PTL 1: International Publication No. WO2018/034178
PTL 2: International Publication No. WO2018/198310
PTL 3: Japanese Patent Application Laid-Open No. 2005-339265

SUMMARY OF INVENTION

Technical Problem

Acoustic characteristics acquired by a wearable device such as described in Patent Literature 1 may change depending on the wearing state. Since changes in acoustic characteristics due to such factors may affect authentication accuracy, a feature extraction method that is robust to differences in the wearing state is required.

The disclosure intends to provide an information processing device, an information processing method, and a storage medium capable of extracting feature quantities robust to differences in the wearing state.

Solution to Problem

According to one example aspect of the disclosure, provided is an information processing device comprising an acquisition unit configured to acquire acoustic characteristics in a frequency domain based on a sound wave propagating in a head of a user and an extracting unit configured to generate a first frequency response function having a rational polynomial equation to extract feature quantity used for biometric authentication of the user based on the first frequency response function, the rational polynomial equation including terms indicating feature of a peak of the acoustic characteristics in a denominator and terms indicating feature of a notch of the acoustic characteristics in a numerator.

According to another example aspect of the disclosure, provided is an information processing method comprising acquiring acoustic characteristics in a frequency domain based on a sound wave propagating in a head of a user; and generating a first frequency response function having a rational polynomial equation to extract feature quantity used for biometric authentication of the user based on the first frequency response function, the rational polynomial equation including terms indicating feature of a peak of the acoustic characteristics in a denominator and terms indicating feature of a notch of the acoustic characteristics in a numerator.

According to another example aspect of the disclosure, provided is a storage medium storing a program that causes a computer to perform acquiring acoustic characteristics in a frequency domain based on a sound wave propagating in a head of a user and generating a first frequency response function having a rational polynomial equation to extract feature quantity used for biometric authentication of the user based on the first frequency response function, the rational polynomial equation including terms indicating feature of a peak of the acoustic characteristics in a denominator and terms indicating feature of a notch of the acoustic characteristics in a numerator.

Advantageous Effects of Invention

According to the disclosure, an information processing device, an information processing method, and a storage medium that can extract feature quantities robust to differences in the wearing state.

DESCRIPTION OF EMBODIMENTS

Example embodiments of the disclosure will be described below with reference to the drawings. Throughout the drawings, the same components or corresponding components are labeled with the same references, and the description thereof may be omitted or simplified.

First Example Embodiment

An information processing system according to the embodiment will be described. The information processing system of the embodiment is a system for performing biometrics authentication using a wearable device such as an earphone.

Figure 1:
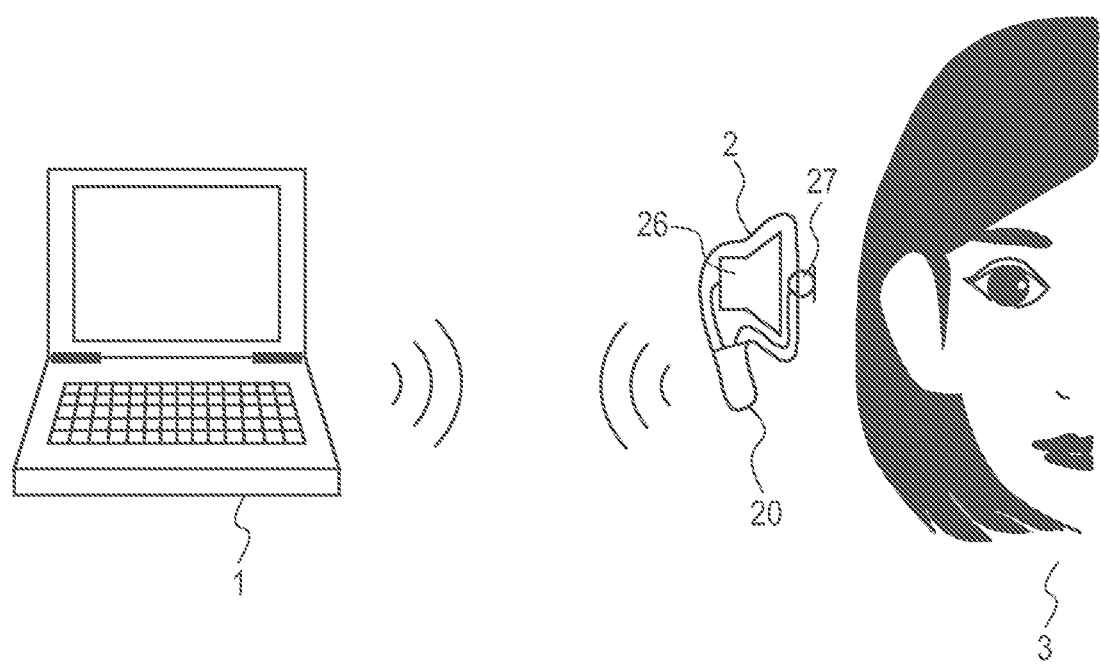
FIG. 1 is a schematic diagram illustrating an overall configuration of an information processing system according to a first example embodiment.

FIG. 1 is a schematic diagram illustrating the overall configuration of an information processing system according to the embodiment. The information processing system includes an information communication device 1 and an earphone 2 which may be wirelessly connected to each other.

The earphone 2 includes an earphone control device 20, a speaker 26, and a microphone 27. The earphone 2 is an acoustic device which can be attached to the head of the user 3, especially to the ear, and is typically a wireless earphone, a wireless headset, or the like. The speaker 26 functions as a sound wave generating unit for emitting sound waves toward the ear canal of the user 3 when the user wears the earphone 2, and is arranged on the wearing surface side of the earphone 2. The microphone 27 is arranged on the mounting surface side of the earphone 2 so as to receive sound waves reflected by the ear canal or the like when the user 3 wears the earphone 2. The earphone control device 20 controls a speaker 26 and a microphone 27 and communicates with an information communication device 1.

Note that, in the specification, "sounds" such as sound waves and voices include non-audible sounds whose frequency or sound pressure level is outside the audible range.

The information communication device 1 is, for example, a computer communicably connected to the earphone 2 and performs biometric authentication based on acoustic information. The information communication device 1 further controls the operation of the earphone 2, transmits sound data for generating sound waves emitted from the earphone 2, and receives sound data acquired from sound waves received by the earphone 2. As a specific example, when the user 3 listens to music using the earphone 2, the information communication device 1 transmits compressed data of the music to the earphone 2. When the earphone 2 is a telephone device for business command in an event hall, a hospital, or the like, the information communication device 1 transmits audio data of the business instruction to the earphone 2. In this case, the audio data of the utterance of the user 3 may be further transmitted from the earphone 2 to the information communication device 1.

Note that, the overall configuration is an example, and for example, the information communication device 1 and the earphone 2 may be connected by wire. Further, the information communication device 1 and the earphone 2 may be configured as an integrated device, and further another device may be included in the information processing system.

Figure 2:
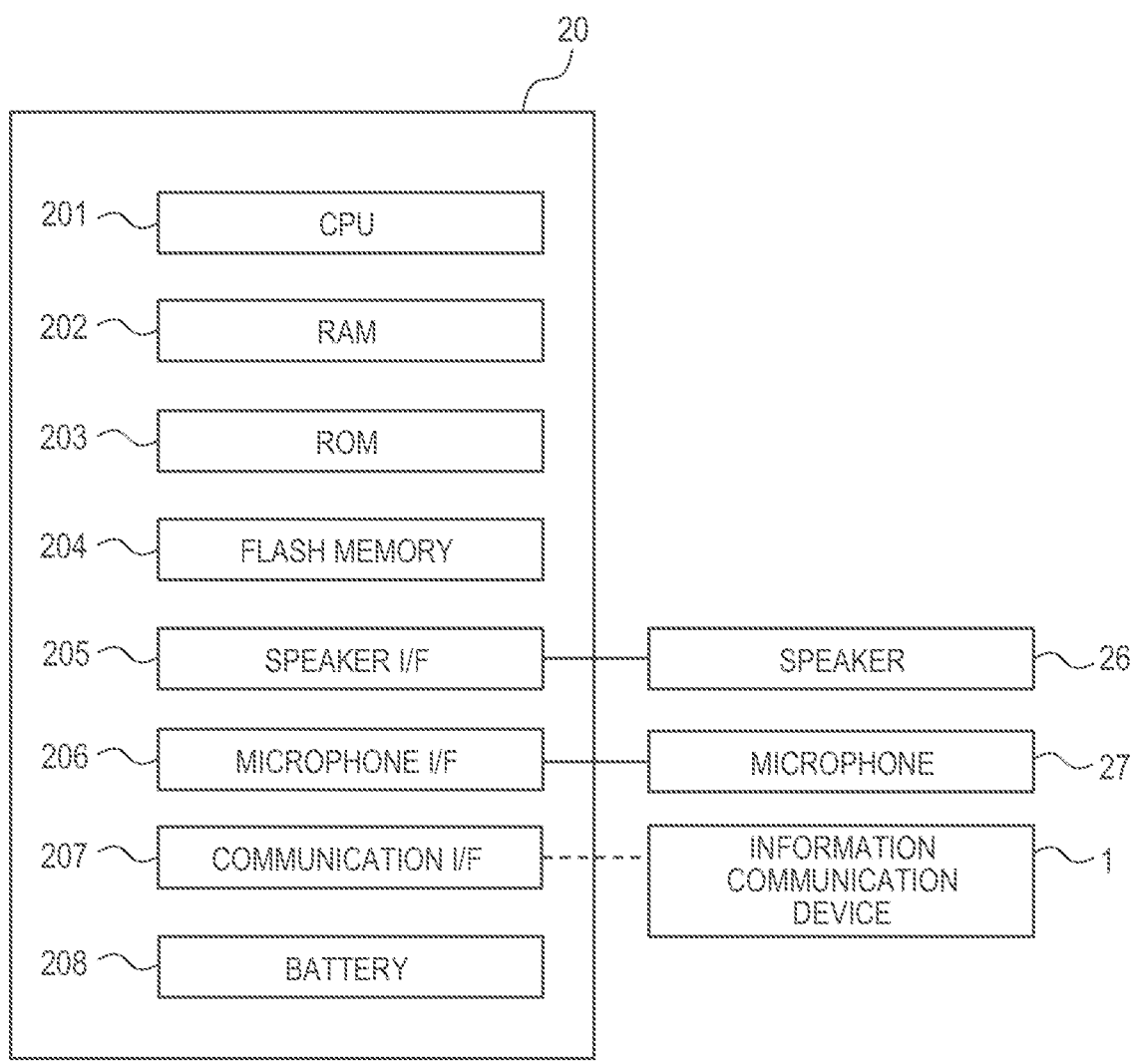
FIG. 2 is a block diagram illustrating a hardware configuration of the earphone control device according to the first embodiment.

FIG. 2 is a block diagram illustrating the hardware configuration of the earphone control device 20. The earphone control device 20 includes a central processing unit (CPU) 201, a random access memory (RAM) 202, a read only memory (ROM) 203, and a flash memory 204. The earphone control device 20 also includes a speaker interface (I/F) 205, a microphone I/F 206, a communication I/F 207, and a battery 208. Each unit of the earphone control device 20 is connected to each other via a bus, wiring, a driving device, or the like (not shown).

The CPU 201 is a processor that has a function of performing a predetermined operations according to programs stored in the ROM 203, the flash memory 204, and the like, and also controlling each unit of the earphone control device 20. The RAM 202 comprises a volatile storage medium and provides a temporary memory area required for the operation of the CPU 201. The ROM 203 comprises a nonvolatile storage medium and stores necessary information such as a program used for the operation of the earphone control device 20. The flash memory 204 comprises a nonvolatile storage medium, and is a storage device for temporarily storing data, storing an operation program of the earphone control device 20, and the like.

The communication I/F 207 is a communication interface based on standards such as Bluetooth (registered trademark) and Wi-Fi (registered trademark), and is a module for communicating with the information communication device 1.

The speaker I/F 205 is an interface for driving the speaker 26. The speaker I/F 205 includes a digital-to-analog conversion circuit, an amplifier, and the like. The speaker I/F 205 converts the audio data into an analog signal and supplies the analog signal to the speaker 26. Thus, the speaker 26 emits sound waves based on the audio data.

The microphone I/F 206 is an interface for acquiring a signal from the microphone 27. The microphone I/F 206 includes an analog-to-digital conversion circuit, an amplifier, and the like. A microphone I/F 206 converts an analog signal generated by sound waves received by the microphone 27 into a digital signal. Thus, the earphone control device 20 acquires audio data based on the received sound waves.

The battery 208 is, for example, a secondary battery, and supplies the power necessary for the operation of the earphone 2. Thus, the earphone 2 can operate wirelessly without being connected to an external power source by wire.

Note that the hardware configuration illustrated in FIG. 2 is an example, and other devices may be added or some devices may not be provided. Some devices may be replaced with other devices having similar functions. For example, the earphone 2 may further include an input device such as a button so as to be able to receive an operation by the user 3, and may further include a display device such as a display and a display lamp for providing information to the user 3. As described above, the hardware configuration illustrated in FIG. 2 can be appropriately changed.

Figure 3:
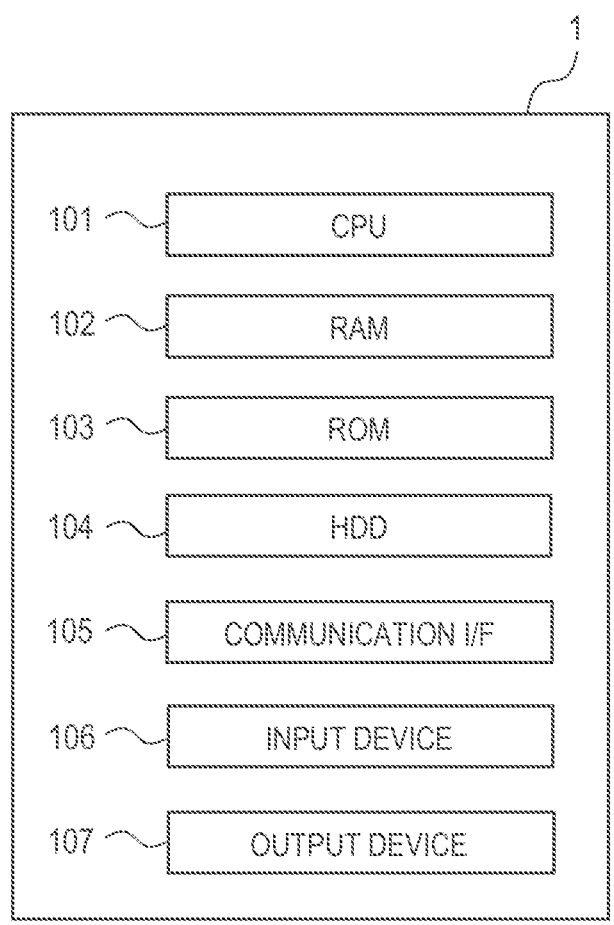
FIG. 3 is a block diagram illustrating a hardware configuration of the information communication device according to the first embodiment.

FIG. 3 is a block diagram illustrating the hardware configuration of the information communication device 1. The information communication device 1 includes a CPU 101, a RAM 102, a ROM 103, and an HDD (Hard Disk Drive) 104. The information communication device 1 also includes a communication I/F 105, an input device 106, and an output device 107. Each unit of the information communication device 1 is connected to each other via a bus, wiring, driving device, or the like (not shown).

In FIG. 3, while each unit constituting the information communication device 1 is illustrated as an integrated device, a part of these functions may be provided by an external device. For example, the input device 106 and the output device 107 may be external devices other than the unit constituting the functions of the computer including the CPU 101 and the like.

The CPU 101 is a processor that has a function of performing predetermined operations according to programs stored in the ROM 103, the HDD 104, and the like, and also controlling each unit of the information communication device 1. The RAM 102 comprises a volatile storage medium and provides a temporary memory area required for the operation of the CPU 101. The ROM 103 comprises a nonvolatile storage medium and stores necessary information such as a program used for the operation of the information communication device 1. The HDD 104 is composed of a nonvolatile storage medium, and is a storage device for temporarily storing data to be transmitted to and received from the earphone 2, storing an operation program of the information communication device 1, and the like.

The communication I/F 105 is a communication interface based on standards such as Bluetooth (registered trademark) and Wi-Fi (registered trademark), and is a module for communicating with other devices such as the earphone 2.

The input device 106 is a keyboard, a pointing device, or the like, and is used for the user 3 to operate the information communication device 1. Examples of the pointing device include a mouse, a trackball, a touch panel, a pen tablet, and the like.

The output device 107 is, for example, a display device. The display device is a liquid crystal display, an OLED (Organic Light Emitting Diode) display, or the like, and is used for displaying information, a GUI (Graphical User Interface) for operation input, or the like. The input device 106 and the output device 107 may be integrally formed as a touch panel.

Note that the hardware configuration illustrated in FIG. 3 is an example, and other devices may be added or some devices may not be provided. Some devices may be replaced with other devices having similar functions. Furthermore, some of the functions of the embodiment may be provided by other devices via a network, and the functions of the embodiment may be implemented by being distributed among a plurality of devices. For example, the HDD 104 may be replaced with a solid state drive (SSD) using a semiconductor memory, or may be replaced with a cloud storage. As described above, the hardware configuration illustrated in FIG. 3 can be appropriately changed.

Figure 4:
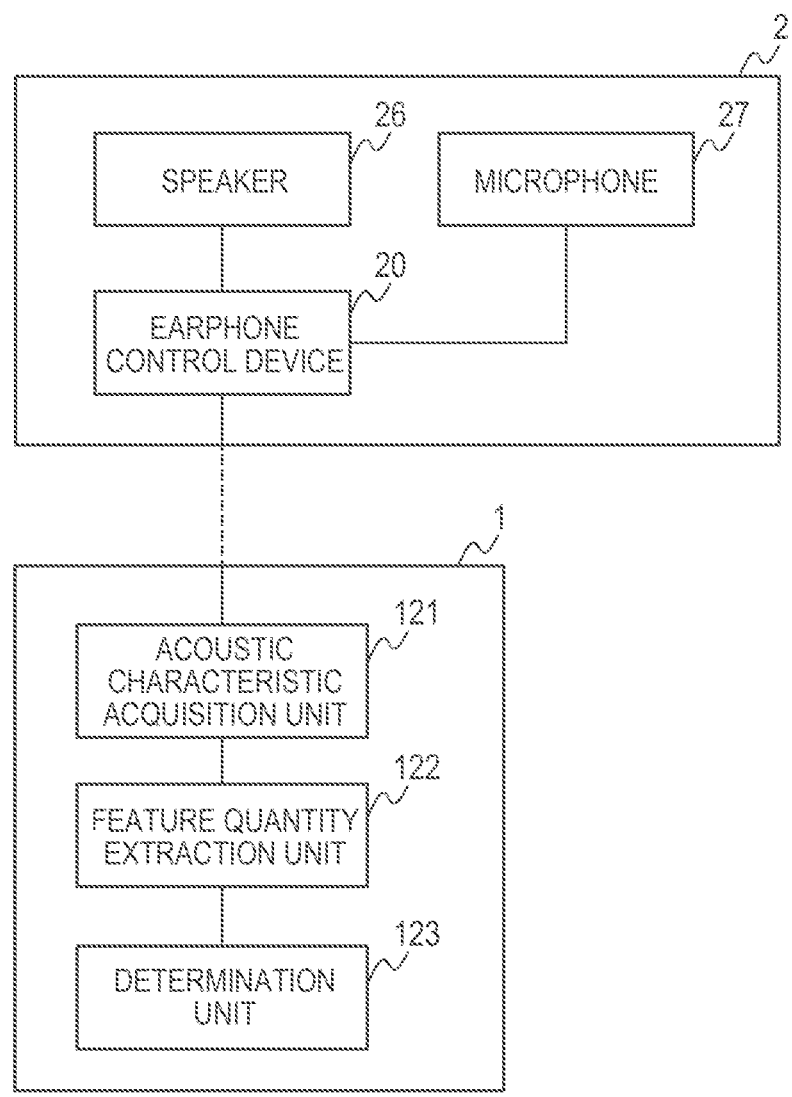
FIG. 4 is a functional block diagram illustrating the earphone and the information communication device according to the first embodiment.

FIG. 4 is a functional block diagram illustrating the earphone 2 and the information communication device 1 according to the embodiment. The information communication device 1 includes an acoustic characteristic acquisition unit 121, a feature quantity extraction unit 122, and a determination unit 123. The structure of the block diagram of the earphone 2 is the same as that of FIG. 2, and therefore a description thereof will be omitted. Note that the acoustic characteristic acquisition unit 121 may be more commonly referred to as an acquisition unit, and the feature quantity extraction unit 122 may be more commonly referred to as an extraction unit.

The CPU 101 loads a program stored in the ROM 103, the HDD 104, or the like into the RAM 102 and executes the program, thereby performing predetermined arithmetic processing. The CPU 101 controls each unit of the information communication device 1 such as the communication OF 105 based on the program. Thus, the CPU 101 realizes the functions of the acoustic characteristic acquisition unit 121, the feature quantity extraction unit 122, and the determination unit 123. The details of the specific processing performed by each functional unit will be described later.

In FIG. 4, some or all of the functions of the function units described in the information communication device 1 may be provided in the earphone control device 20 instead of the information communication device 1. That is, the above-described functions may be realized by the information communication device 1, the earphone control device 20, or the information communication device 1 and the earphone control device 20 may cooperate with each other. The information communication device 1 and the earphone control device 20 may be more generally referred to as an information processing device. In the following description, each functional unit relating to acquisition and determination of acoustic information is assumed to be provided in the information communication device 1, as shown in FIG. 4, unless otherwise noted.

Figure 5:
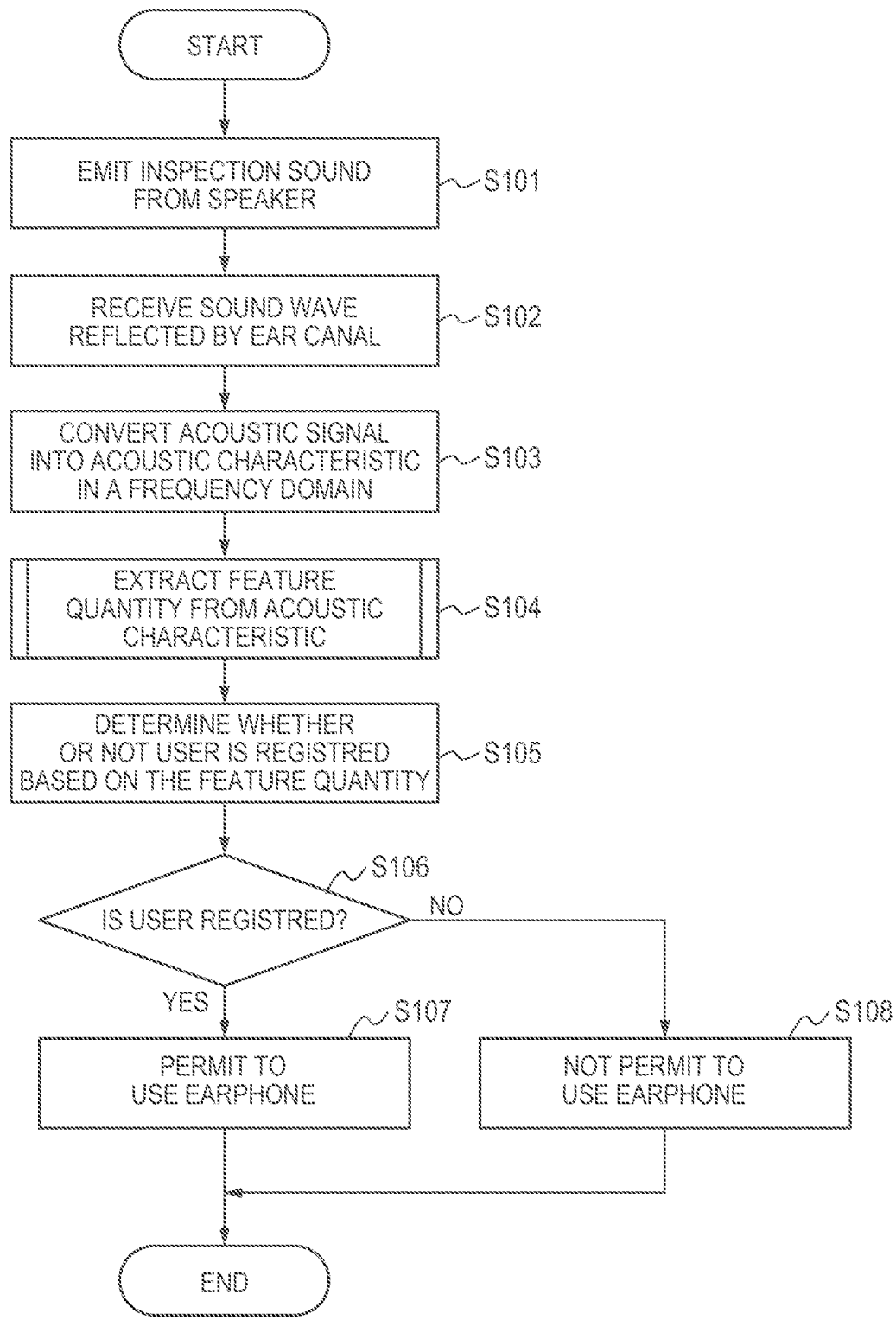
FIG. 5 is a flowchart illustrating an outline of the biometric authentication processing performed by the information communication device according to the first embodiment.

FIG. 5 is a flowchart illustrating the outline of the biometric authentication processing performed by the information communication device 1 according to the embodiment. The operation of the information communication device 1 will be described with reference to FIG. 5.

The biometric authentication processing illustrated in FIG. 5 is executed, for example, when the user 3 operates the earphone 2 to start using the earphone 2. Alternatively, the biometric authentication process illustrated in FIG. 5 may be executed every time a predetermined time elapses when the earphone 2 is powered on.

In step S101, the acoustic characteristic acquisition unit 121 instructs the earphone control device 20 to emit an inspection sound. The earphone control device 20 transmits an inspection signal to a speaker 26, and the speaker 26 emits an inspection sound generated based on the inspection signal to the ear canal of a user 3.

A signal including a predetermined range of frequency components such as a chirp signal, an M-sequence (maximum length sequence) signal, white noise, and an impulse signal may be used as the inspection signal. Thus, an acoustic signal including information within a predetermined range of frequency can be acquired. The inspection sound may be an audible sound in which the frequency and sound pressure level are within an audible range. In this case, the user 3 can be notified that authentication is performed by making the user 3 perceive sound waves at the time of authentication. The inspection sound may be a non-audible sound whose frequency or sound pressure level is outside the audible range. In this case, comfort in use is improved because it is possible to make the sound waves hard to be perceived by the user 3.

In step S102, the microphone 27 receives the sound wave reflected by the ear canal (otoacoustic) or the like and converts the sound wave reflected by the ear canal into an electrical signal in the time domain. This electrical signal is sometimes referred to as an acoustic signal. The microphone 27 transmits the acoustic signal to the earphone control device 20, and the earphone control device 20 transmits the acoustic signal to the information communication device 1.

In step S103, the acoustic characteristic acquisition unit 121 acquires acoustic characteristics of a frequency domain based on sound waves propagating in the head of the user. This acoustic characteristic may be, for example, a frequency spectrum acquired by converting an acoustic signal in a time domain into a frequency domain using an algorithm such as fast Fourier transform. The acquired acoustic characteristics are stored in the HDD 104.

In step S104, the feature quantity extraction unit 122 extracts the feature quantity from the acoustic characteristic. The details of this processing will be described later. The extracted feature quantity is stored in an HDD 104 and used for biometric authentication.

In step S105, the determination unit 123 determines whether or not the user 3 is a registrant by comparing the feature quantity extracted by the feature quantity extraction unit 122 with the preregistered feature quantity of the registrant stored in the HDD 104. If it is determined that the user 3 is the registrant (YES in step S106), the process proceeds to step S107. If it is determined that the user 3 is not the registrant (NO in step S106), the process proceeds to step S108.

In step S107, the information communication device 1 transmits a control signal indicating that the use of the earphone 2 by the user 3 is permitted to the earphone 2. Thus, the earphone 2 becomes usable by the user 3.

In step S108, the information communication device 1 transmits a control signal indicating that the use of the earphone 2 by the user 3 is not permitted to the earphone 2. Thus, the earphone 2 becomes unusable by the user 3. The unusable state may be, for example, a state in which no sound is emitted from the speaker 26 of the earphone 2. The control in steps S107 and S108 does not control the earphone 2, but may control the information communication device 1. For example, the state of communication connection between the information communication device 1 and the earphone 2 may be changed between the use permitted state and the use not permitted state.

In step S105, the determination unit 123 may further determine whether or not the user 3 wears the earphone 2 in the ear of the user 3 based on the acoustic characteristics or the feature quantity. When it is determined that the user 3 does not wear earphone in the ear of the user 3, the processing for disallowing the use of the earphone 2 can be performed as in the case where it is determined that the user 3 is not a registrant.

Figure 6:
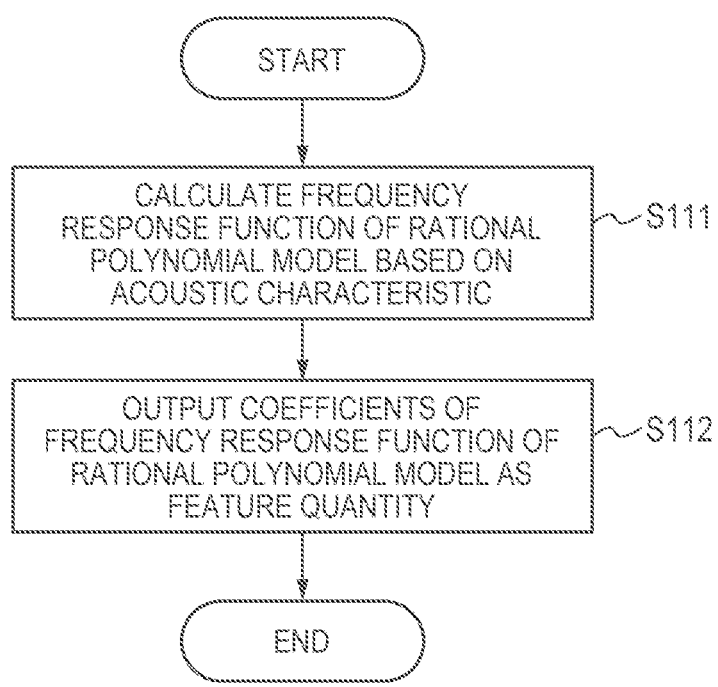
FIG. 6 is a flowchart illustrating the feature quantity extraction processing performed by the information communication device according to the first embodiment.

FIG. 6 is a flowchart illustrating the feature quantity extraction processing performed by the information communication device 1 according to the embodiment. Referring to FIG. 6, the feature quantity extraction process in step S104 of FIG. 5 will be described in more detail.

In step S111, the feature quantity extraction unit 122 calculates the frequency response function of the rational polynomial model based on the acoustic characteristics acquired by the acoustic characteristic acquisition unit 121. The acoustic characteristics and the frequency response function of the rational polynomial model are explained. The frequency response function of the rational polynomial model is sometimes called a first frequency response function.

Figure 7:
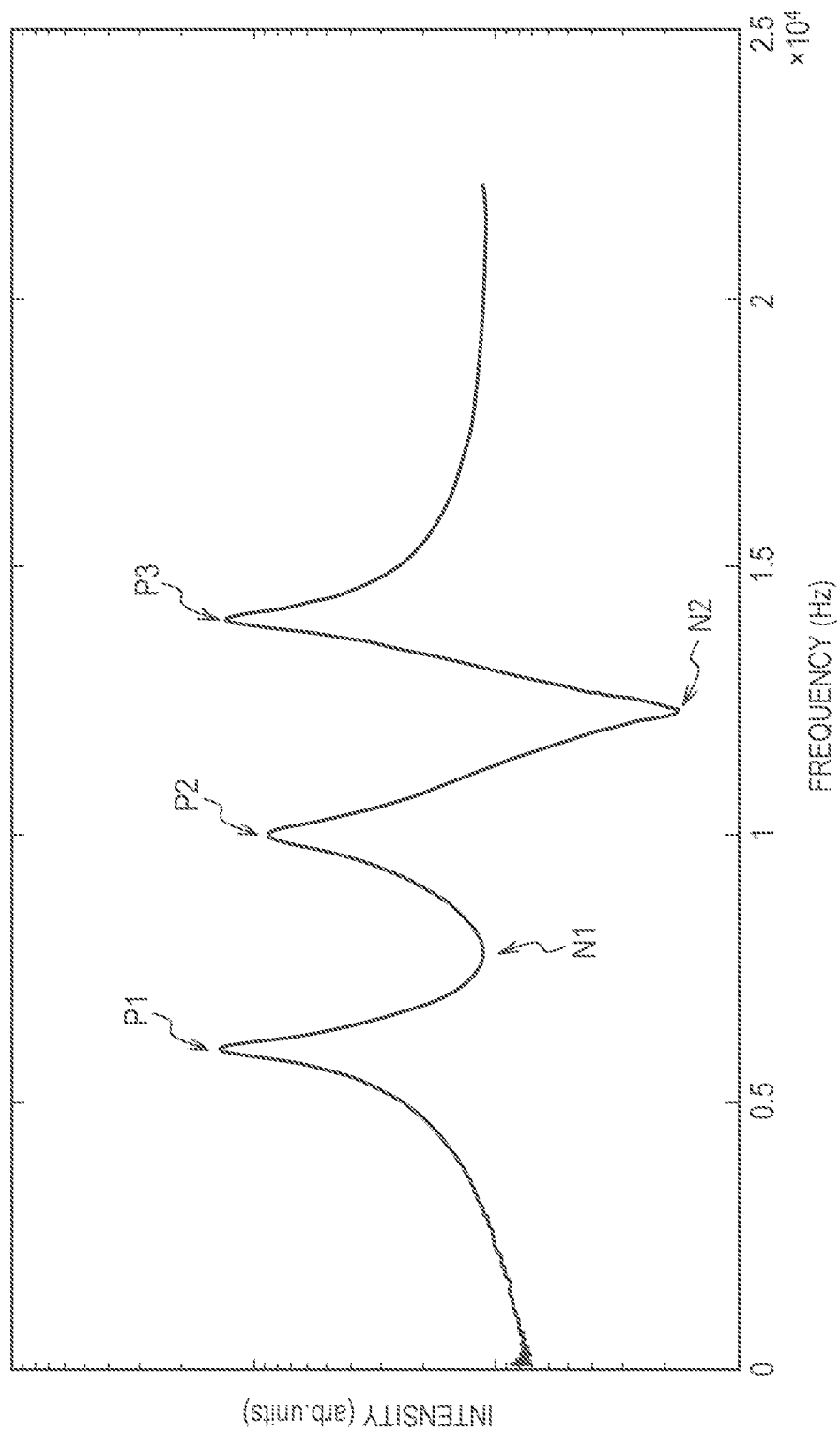
FIG. 7 is a graph illustrating an example of the measurement of acoustic characteristics.

FIG. 7 is a graph illustrating an example of measurement of acoustic characteristics acquired by the acoustic characteristic acquisition unit 121. In FIG. 7, the horizontal axis indicates the frequency, and the vertical axis indicates the intensity of the signal in an arbitrary unit. The vertical axis is displayed on a logarithmic scale. This intensity indicates, for example, the intensity of the sound wave received by the microphone 27. Hereinafter, the acoustic characteristic is acquired by normalizing the intensity of the sound wave received by the microphone 27 with the intensity of the sound wave emitted from the speaker 26.

As shown in FIG. 7, the acquired acoustic characteristic has a plurality of peaks (maximum points) P1, P2, P3 and a plurality of notches (minimum points) N1, N2. Peaks P1, P2, P3 and notches N1, N2 indicate resonances occurring in the air column formed by the canal of user 3, the tympanic membrane of the user 3, and the earphone 2. Since a plurality of peaks P1, P2, P3 and notches N1, N2 are observed, it is understood that a plurality of resonance modes exist. For example, each of the peaks P1, P2, and P3 indicates a resonance mode in which the amplitude of the sound wave increases at the position of the microphone 27 of the earphone 2. In addition to the resonance in the air column, a resonance mode in the earphone 2 can be observed. Since the properties of the peaks P1, P2, P3 and the notches N1, N2 depend on the shape of the ear canal of the user 3, it is effective for extracting the feature quantity for identifying the individual.

Such acoustic characteristics can be expressed by a frequency response function based on a rational polynomial model shown in the following equation (1).

[Math. 1]

$$\frac{\sum_{i=0}^{2N_m} \Omega_1(\omega)\beta_i}{\sum_{i=0}^{2N_m} \Omega_1(\omega)\alpha_i} \quad (1)$$

where $\omega$ is the angular frequency. $\Omega_l(\omega)$ is a basis function in the polynomial expansion, and this basis function is independent of the subject whose acoustic characteristics were acquired. $\Omega_l(\omega)$ is a complex function. $\alpha_l$ and $\beta_l$ are the real coefficients of the polynomial, and this term varies depending on subject. Namely, $\alpha_l$ and $\beta_l$ are feature quantities indicating the feature of the subject. $N_m$ is the number of modes assumed in the rational polynomial model, and the index 1 is an argument indicating each mode.

The denominator of the equation (1) becomes zero at the frequency where the peak of the intensity occurs, and the numerator of the equation (1) becomes zero at the frequency where the notch of the intensity occurs. Thus, in the frequency response function based on the rational polynomial model, the peak features are considered in the denominator, and the notch features are considered in the numerator. A feature quantity extraction unit 122 determines coefficients $\alpha_l$ and $\beta_l$ so as to approximate the acquired acoustic characteristic by the equation (1) to estimate the frequency response function. For this approximation, an approximation method such as the least squares method, the maximum likelihood estimation method, and the like, including an algorithm such as the minimization of the error function, may be used.

In step S112, the feature quantity extraction unit 122 outputs the coefficients $\alpha_l$ and $\beta_l$ of the frequency response function based on the rational polynomial model as the feature quantity indicating the user 3. In the output of the feature quantity, coefficients $\alpha_l$ and $\beta_l$ may be extracted for a plurality of $N_m$ different from each other, and coefficients $\alpha_l$ and $\beta_l$ acquired in the plurality of $N_m$ may be combined to extract as the feature quantity. Thus, the properties of the peaks and notches stably acquired in the plurality of $N_m$ can be reflected in the feature quantity.

Since the coefficients $\alpha_l$ and $\beta_l$ need not be processed to calculate logarithms at the time of derivation, coefficients $\alpha_l$ and $\beta_l$ are feature quantities that are robust to differences in the wearing state. Details of this will be described later.

The effect of the above-described feature quantity extraction method will be described. As described above, the acoustic characteristics include peaks and notches due to resonances occurring in the air column formed by the ear canal of the user 3, the tympanic membrane, and the earphone 2. Since the frequency and magnitude of these peaks and notches depend on the shape of the air column, they can vary depending on the position of the earphone 2. Therefore, the acoustic characteristics may change depending on the wearing state of the earphone 2.

Figure 8:
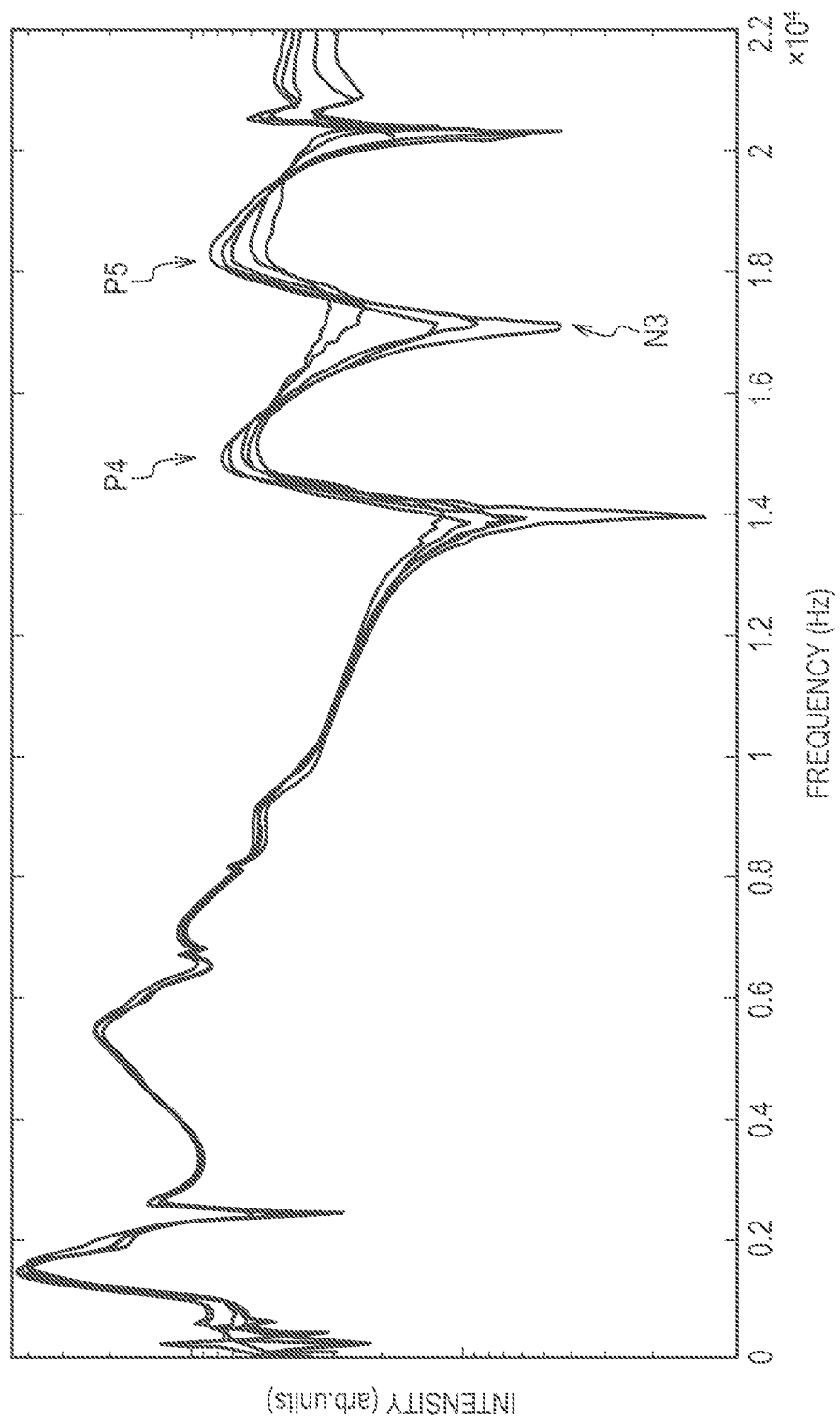
FIG. 8 is a graph illustrating an example of changes in acoustic characteristics when the earphone is repeatedly attached and detached.

FIG. 8 is a graph illustrating the example of changes in acoustic characteristics when the earphone 2 is repeatedly attached and detached. In FIG. 8, the acoustic characteristics are acquired five times by changing the wearing state by repeating attachment and detachment, and the acoustic characteristics are superimposed and displayed. Focusing on the peaks P4 and P5 and the notch N3 in FIG. 8, it can be seen that the variation of the notch N3 is larger than that of the peaks P4 and P5.

The reason why the variation of the notch N3 is larger than that of the peaks P4 and P5 will be explained with a simple example. It is assumed that there are only two resonant modes present in the ear canal and that the acoustic characteristics resulting from the two resonant modes can be separated into two, $S_1(f)$ and $S_2(f)$. It is assumed that $S_1(f)$ has a characteristic that a peak occurs at the natural frequency $f_1$, and $S_2(f)$ has a characteristic that a peak occurs at the natural frequency $f_2$. At this time, the acoustic characteristic $S_i(f)$ taking into account the interference of the two modes at the frequency between $f_1$ and $f_2$ satisfies the following equation (2), assuming that the phase difference between the modes is 0.

[Math. 2]

$$|S_i(f)|^2 = |S_1(f)|^2 + |S_2(f)|^2 + 2|S_1(f)||S_2(f)|\cos\theta \quad (2)$$

When the wearing state of the earphone 2 is changed, The acoustic characteristic $|S_i(f)|$ is changed by changing three parameters of $|S_1(f)|$, $|S_2(f)|$ and $\theta$. Since the influence of $S_2(f)$ is sufficiently small at the natural frequency $f_1$, the acoustic characteristic $|S_i(f)|$ may be approximated by the following equation (3).

[Math. 3]

$$|S_i(f)|^2 \approx |S_1(f)|^2 \quad (3)$$

Since the influence of $S_1(f)$ is sufficiently small at the natural frequency $f_2$, the acoustic characteristic $|S_i(f)|$ may be approximated by the following equation (4).

[Math. 4]

$$|S_i(f)|^2 \approx |S_2(f)|^2 \quad (4)$$

Based on equations (3) and (4), the term including θ can be ignored in the vicinity of the natural frequency. Therefore, it can be seen that in the vicinity of the natural frequency, the acoustic characteristic $|S_i(f)|$ is affected by change of the absolute value (power) due to the change of the wearing state, but is not affected by change of the phase difference due to the change of the wearing state. This corresponds to a relatively small fluctuation in the vicinity of the peaks P4 and P5 in FIG. 8. On the other hand, since the above approximation does not hold true at frequencies near the middle of $f_1$ and $f_2$, both the change of the absolute value and the change of the phase difference may be factors for changing the acoustic characteristics. This corresponds to a relatively large fluctuation in the vicinity of the notch N3 in FIG. 8.

As described in Patent Literature 1, the mel-frequency cepstral coefficient has been used as a feature quantity for authentication. The process of deriving the mel-frequency spectral coefficient may include a process of calculating the logarithm of the acoustic characteristic. Converting acoustic properties to a logarithmic scale emphasizes areas of low intensity.

As described above, in the vicinity of the notch, since the phase difference θ between adjacent modes is easily affected, the variation due to the change of the wearing state is remarkable. In addition, conversion to a logarithmic scale emphasizes the effect of variation near the notch where the intensity is minimal. By superimposing these two influences, feature quantity extraction using the mel-frequency cepstral coefficient including the process of calculating the logarithm in the derivation process may be easily affected by changes in the wearing state.

On the other hand, the feature quantity extraction method according to the embodiment is robust against the difference in the wearing state because the processing of the logarithm calculation is not required in the derivation. For the above reasons, in the embodiment, it is possible to extract a feature quantity robust to a difference in the wearing state of the earphone 2 while paying attention to the features of the notch and the peak.

In this embodiment, the feature quantity is extracted from the frequency response function by the rational polynomial model. It will be explained that this processing is a method of extracting feature quantities focusing on features of notches and peaks. The frequency response function based on the rational polynomial model in equation (1) can be converted into a frequency response function based on the pole/residue model shown in equation (5) below. This conversion corresponds to the partial fractional expansion of the frequency response function by the rational polynomial model. The frequency response function of the pole/residue model is sometimes called a second frequency response function.

[Math. 5]

$$\hat{H}(\omega) = \sum_{k=1}^{N_m} \left\{ \frac{R_k}{j\omega - \lambda_k} + \frac{R_k^*}{j\omega - \lambda_k^*} \right\} + C \quad (5)$$

where, $\lambda_k$ is a complex number indicating the pole of the acoustic characteristic, and $R_k$ is a complex number indicating the shape of the pole. $\lambda_k$ and $R_k$ are sometimes called poles and residues, respectively. Note that j is an imaginary unit, C is a remainder term, and "*" is a symbol indicating complex conjugation.

Physically, $\lambda_k$ includes information about the pole's natural frequency $f_k$ and the pole's attenuation ratio $\zeta_k$. The natural frequency $f_k$ and the attenuation ratio $\zeta_k$ of the pole are represented by the following equations (6) and (7), respectively. Here, Re(4) is the real part of $\lambda_k$, and Im($\lambda_k$) is the imaginary part of $\lambda_k$.

[Math. 6]

$$f_k = \frac{\text{Im}(\lambda_k)}{2\pi} \quad (6)$$

[Math. 7]

$$\zeta_k = -\frac{\text{Re}(\lambda_k)}{|\lambda_k|} \quad (7)$$

At the natural frequency, the imaginary part of the term $j\omega-\lambda_k$ in parentheses in equation (5) becomes zero, and the real part of the term $j\omega-\lambda_k$ becomes a constant determined by the attenuation ratio $\zeta_k$. Therefore, the term in parentheses in equation (5) is a function of the damped oscillation representing the k-th peak. In other words, equation (5) expresses the frequency response function by the sum of $N_m$ damping vibrations.

In this way, the frequency response function based on the rational polynomial model of equation (1) can be converted into a frequency response function based on the pole/residue model composed of the sum of the damping vibrations. Therefore, the frequency response function based on the rational polynomial model substantially includes features of the resonance mode, and is suitable for feature quantity extraction focusing on features of peaks and notches of the resonance mode.

Note that the feature quantity may be extracted from the term included in the frequency response function of the pole/residue model instead of the rational polynomial model. However, since the respective terms of the pole/residue model vary depending on the subject, it is difficult to determine the terms to be compared at the time of matching the feature quantity, while the basis function of the rational polynomial model does not depend on the user, so that there is an advantage that comparison is easy at the time of matching the feature quantity. Therefore, it is desirable to extract the feature quantity from the term included in the frequency response function of the rational polynomial model.

Second Example Embodiment

The information processing system of the embodiment differs from the first embodiment in the content of the feature quantity extraction processing, but is similar to the first embodiment in other parts. In the following, differences from the first embodiment will be mainly described, and descriptions of common portions will be omitted or simplified.

Figure 9:
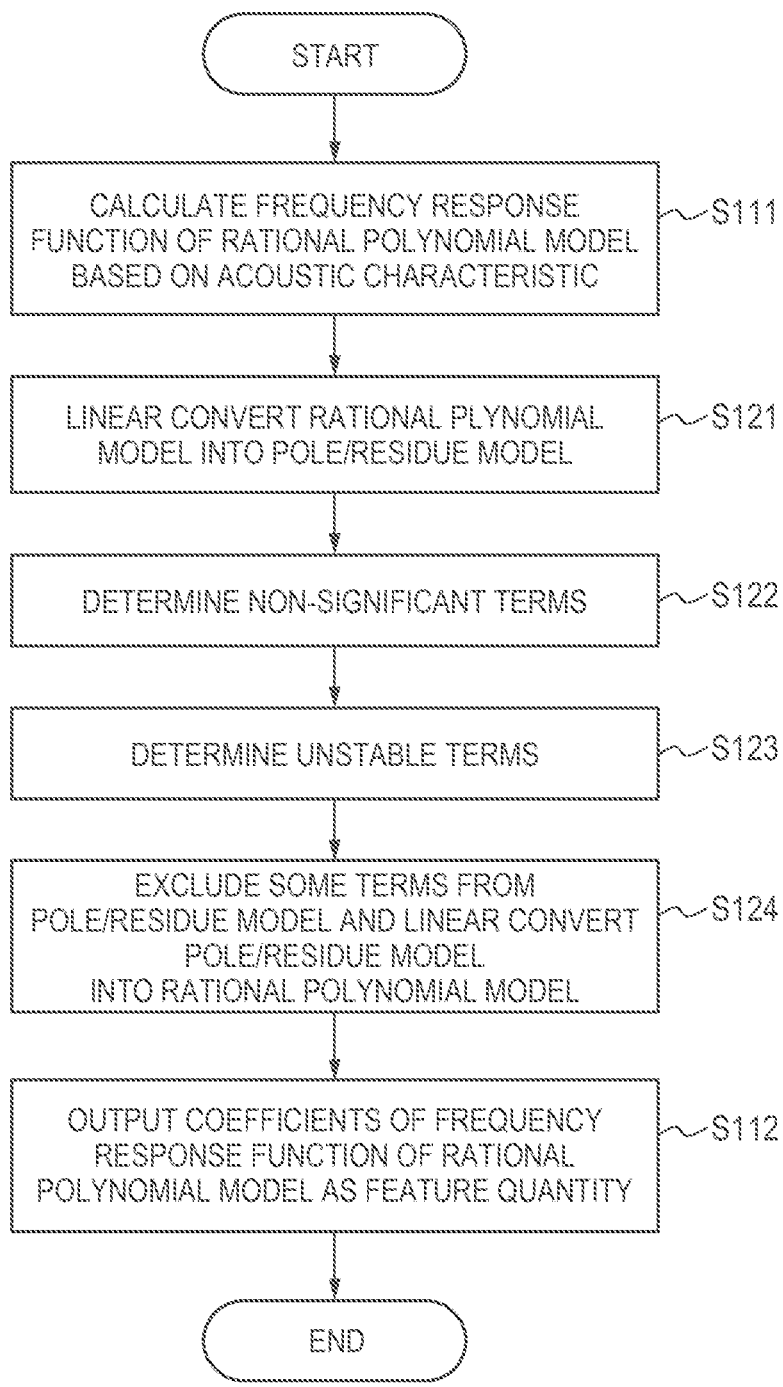
FIG. 9 is a flowchart illustrating the feature quantity extraction processing performed by the information communication device according to the second embodiment.

FIG. 9 is a flowchart illustrating feature quantity extraction processing performed by the information communication device 1 according to the embodiment. This embodiment is different from the first embodiment in that a process of converting a rational polynomial model into a pole/residue model and excluding some terms is added.

In step S111, the feature quantity extraction unit 122 calculates the frequency response function of the rational polynomial model as in the first embodiment.

In step S121, the feature quantity extraction unit 122 converts the frequency response function of the rational polynomial model into the frequency response function of the pole/residue model. The contents of this process are as described in the first embodiment using equations (1), (5), and the like, and therefore the description thereof will be omitted.

In step S122, the feature quantity extraction unit 122 determines a non-significant term from the respective terms of the frequency response function of the pole/residue model. Non-significant terms are the terms that clearly do not adequately represent the damped oscillations due to the physical phenomenon of resonance in the ear canal. Specifically, there are terms such as a term in which the attenuation ratio $\zeta_k$ is negative, a term in which the natural frequency $f_k$ is outside the frequency range in which resonance may occur, and so on, which are clearly contrary to the physical phenomenon of resonance in the ear canal.

In step S123, the feature quantity extraction unit 122 determines an unstable term from the respective terms in the frequency response function of the pole/residue model. The unstable terms are the term that do not appear stably when processing for approximating acoustic characteristics by a frequency response function is performed several times by changing a calculation condition such as an approximation condition. For example, a term that does not have the same natural frequency and the same attenuation ratio when the number of modes $N_m$ considered in a model such as that shown in equations (1) or (5) is an unstable term. As a specific example of the method for determining the unstable term, a method for determining a mode in which the change amount of the natural frequency or the attenuation ratio exceeds a predetermined error range in the case where the number of modes to be considered is $N_a$ or $N_a+1$ is mentioned as the unstable mode. Such an unstable term does not represent the physical phenomenon of resonance in the ear canal, but is likely to be a pseudo one caused by computational factors.

In step S124, the feature quantity extraction unit 122 excludes some terms from the frequency response function of the pole/residue model to convert them into the frequency response function of the rational polynomial model. Here, "some terms" can be non-significant terms extracted in step S122 and unstable terms extracted in step S123. The terms that do not adequately represent physical phenomena are excluded. Further, since it is not necessary to extract the remainder term C as the feature quantity indicating the feature of the user 3, "some term" may include the remainder term C. Specifically, the process of excluding some of the terms may be a process of changing the value of the residue $R_k$ or the remainder term C of the corresponding term to zero.

In step S112, the feature quantity extraction unit 122 outputs the coefficient of the frequency response function of the rational polynomial model obtained in step S124 as the feature quantity by the same processing as in the first embodiment.

According to the technique of the embodiment, it is possible to extract a feature quantity robust to a difference in the wearing state as in the first embodiment. Further, since the feature quantity is extracted after excluding the non-significant term, the unstable term, and the like, the feature quantity more appropriately reflecting the biological feature such as the shape of the ear canal of the user 3 can be extracted.

Third Example Embodiment

The information processing system of the embodiment differs from the first and second embodiments in the content of the feature quantity extraction processing, but is similar to the first and second embodiments in other parts. In the following, differences from the second embodiment will be mainly described, and descriptions of common portions will be omitted or simplified.

Figure 10:
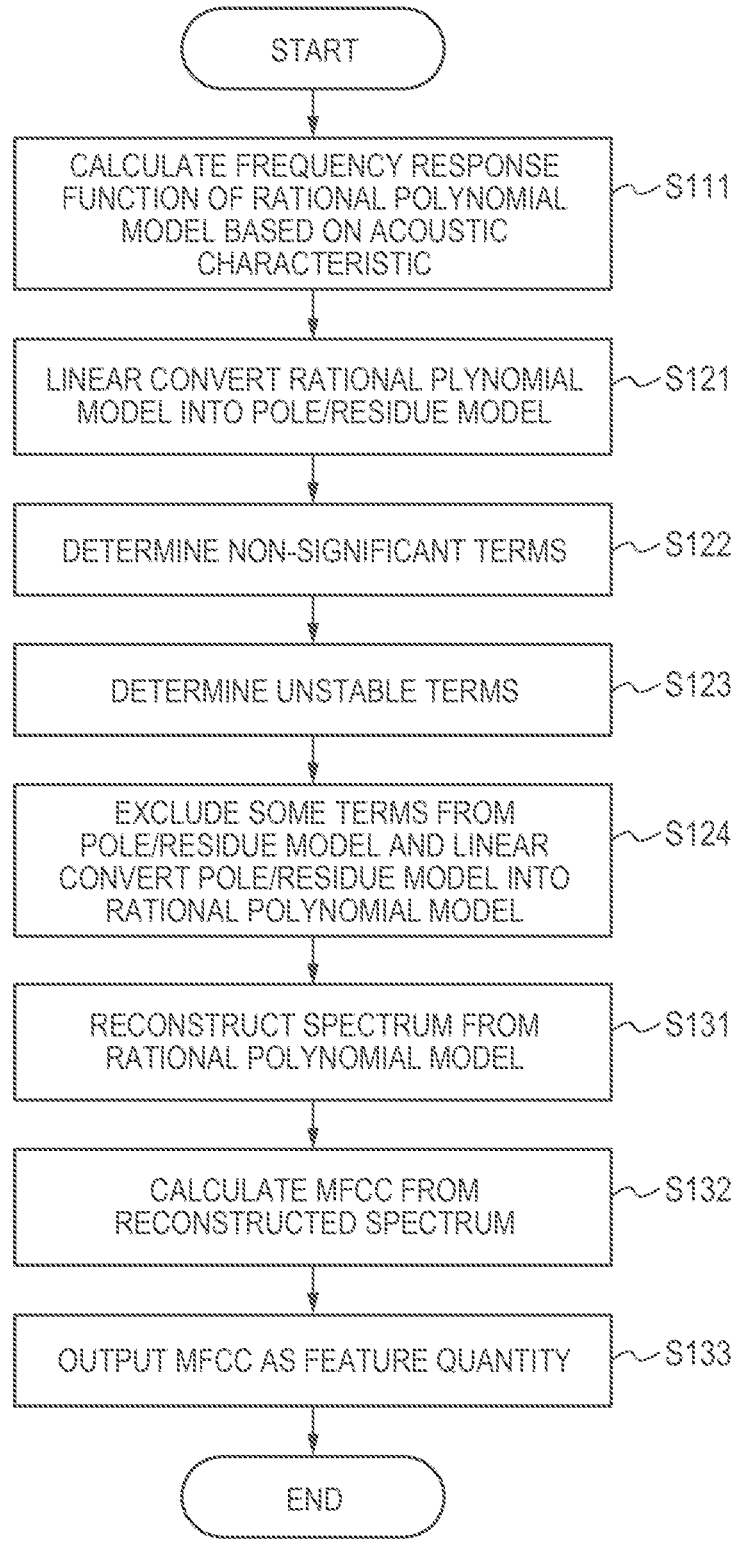
FIG. 10 is a flowchart illustrating the feature quantity extraction processing performed by the information communication device according to the third embodiment.

FIG. 10 is a flowchart illustrating the feature quantity extraction processing performed by the information communication device 1 according to the embodiment. This embodiment is different from the second embodiment in that a process for calculating a mel-frequency cepstral coefficient (MFCC) by reconstructing a spectrum from a frequency response function of a rational polynomial model obtained by excluding some terms is added.

The processes from step S111 to step S124 are the same as those in the second embodiment, and therefore the description thereof will be omitted.

In step S131, the feature quantity extraction unit 122 reconstructs the spectrum of the acoustic characteristic from the frequency response function of the rational polynomial model generated in step S124.

In step S132, the feature quantity extraction unit 122 calculates a mel-frequency cepstral coefficient from the reconstructed spectrum. An example of a method for calculating the mel-frequency cepstral coefficient will be described below.

First, the feature quantity extraction unit 122 applies the mel-filter bank to the reconstructed spectrum. The mel-filter bank is a filter bank including a plurality of triangular window functions. The plurality of triangular window functions are configured such that the higher the frequency, the wider the frequency width, based on a mel-scale considering human auditory characteristics. The spectrum obtained by applying the mel-filter bank is called mel-spectrum. Further, a conversion of the intensity (vertical axis) of the mel-spectrum into a logarithmic scale is called a mel-logarithmic spectrum. By converting to a logarithmic scale, high-order resonance phenomena with small gain can be well represented.

Next, the feature quantity extraction unit 122 performs discrete cosine transformation on the mel-logarithmic spectrum to calculate a cepstrum of a frequency domain. A mel-frequency cepstral coefficient is calculated by extracting a coefficient of a term of the order in a predetermined range among the cepstrums. In this method, it is possible to acquire a feature quantity subjected to efficient compression by weighting considering human auditory characteristics.

In step S133, the feature quantity extraction unit 122 outputs the mel-frequency cepstral coefficient acquired in the process of step S132 as the feature quantity.

According to the technique of the embodiment, as in the second embodiment, it is possible to extract a feature quantity that more appropriately expresses a biological feature such as the shape of the ear canal of the user 3. In addition, since the weighting taking human auditory characteristics into consideration is performed in the calculation process of the mel-frequency cepstral coefficient, the feature quantity subjected to efficient compression can be extracted.

Fourth Example Embodiment

The information processing system of the embodiment differs from the first to third embodiments in the content of the feature quantity extraction processing, but is similar to the first to third embodiments in other parts. In the following, differences from the third embodiment will be mainly described, and descriptions of common portions will be omitted or simplified.

Figure 11:
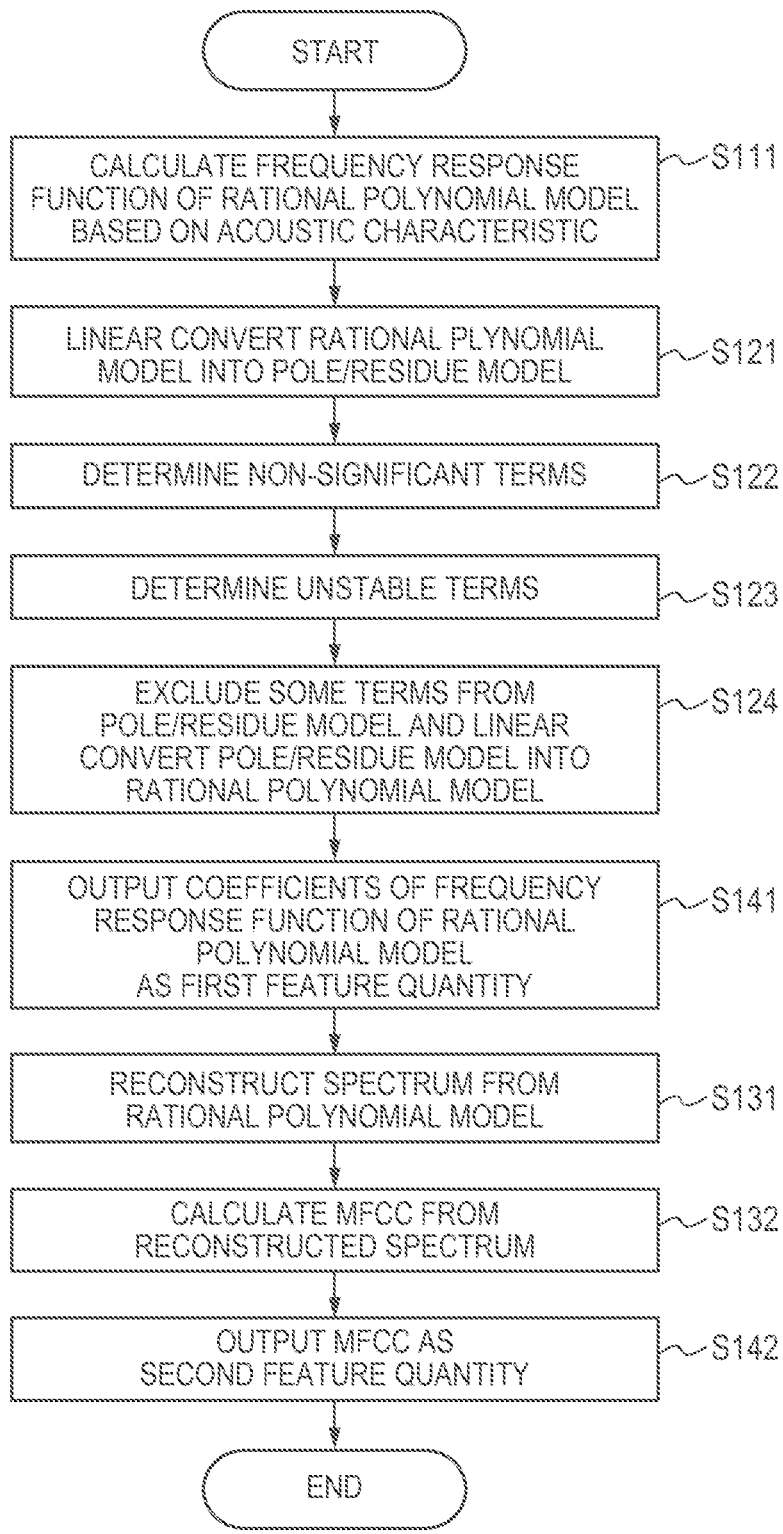
FIG. 11 is a flowchart illustrating the feature quantity extraction processing performed by the information communication device according to the fourth embodiment.

FIG. 11 is a flowchart illustrating the feature quantity extraction processing performed by the information communication device 1 according to the embodiment. This embodiment differs from the second or third embodiment in that both the coefficient of the frequency response function of the rational polynomial model and the mel-frequency cepstral coefficient are extracted as feature quantities.

The processes from step S111 to step S124 are the same as those in the second embodiment, and therefore the description thereof will be omitted.

In step S141, the feature quantity extraction unit 122 outputs the coefficient of the frequency response function of the rational polynomial model acquired in step S124 as the first feature quantity by the same processing as in the first or second embodiment.

The processing in steps S131 and S132 is the same as that in the third embodiment, and therefore the description thereof will be omitted.

In step S142, the feature quantity extraction unit 122 outputs the mel-frequency cepstral coefficient acquired by the process in step S132 as the second feature quantity.

In the determination processing after the feature quantity extraction (step S105 in FIG. 5), it is determined whether or not the user 3 is a registrant based on both the first feature quantity and the second feature quantity. Concretely, a technique can be used in which a first score acquired by collation using the first feature quantity and a second score acquired by collation using the second feature quantity are weighted and added in a predetermined ratio, and whether or not the user 3 is a registrant is determined based on the added score. Further, the collation using the first feature quantity and the collation using the second feature quantity may be performed separately, and the logical sum or logical product of the two collation results may be the final collation result.

According to the technique of the embodiment, since the feature quantity extraction technique according to the second embodiment and the feature quantity extraction technique according to the third embodiment are used together, both effects can be acquired. Further, in the embodiment, since the determination can be performed by using the first feature quantity from which the peak and notch features are extracted and the second feature quantity from which the waveform features of the acoustic characteristics are mainly extracted, a highly accurate biometric authentication in which more multifaceted information is considered can be realized.

The system described in the above embodiment can also be configured as in the following fifth embodiment.

Fifth Example Embodiment

Figure 12:
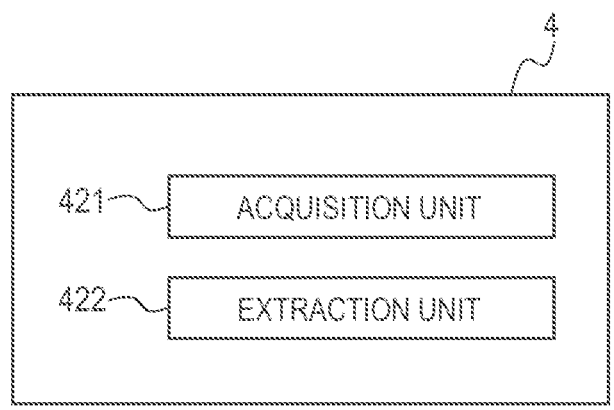
FIG. 12 is a functional block diagram illustrating the information processing device according to the fifth embodiment.

FIG. 12 is a functional block diagram illustrating the information processing device 4 according to the fifth embodiment. The information processing device 4 includes an acquisition unit 421 and an extraction unit 422. The acquisition unit 421 acquires acoustic characteristics of a frequency domain based on sound waves propagating in the head of a user. The extraction unit 422 generates a first frequency response function having a rational polynomial including a term indicating a characteristic of a peak of acoustic characteristics in a denominator, and extracts a feature quantity used for biometric authentication of a user based on the first frequency response function.

According to the embodiment, there is provided an information processing device 4 capable of extracting feature quantities robust to differences in wearing states.

Modified Example Embodiments

The disclosure is not limited to the embodiments described above, and may be modified as appropriate without departing from the spirit of the disclosure. For example, an example in which a part of the configuration of one embodiment is added to another embodiment or an example in which a part of the configuration of another embodiment is replaced is also an embodiment of the disclosure.

In the above-described embodiment, the earphone 2 is exemplified as an example of a wearable device, but the earphone is not limited to an earphone worn in an external ear hole as long as acoustic information necessary for processing can be acquired. For example, the wearable device may be a headphone that covers the entire ear, or a bone-conduction type acoustic device that transmits sound waves indirectly from the head other than the external ear hole. Further, the wearable device may be constituted by two earphones attached to both ears, and in this case, the biometrics of the above-described embodiment may be performed for both ears, and the biometrics of the above-described embodiment may be performed for only one ear.

A processing method in which a program for operating the configuration of the embodiment is recorded in a storage medium so as to realize the function of the embodiment, the program recorded in the storage medium is read out as a code, and is executed in a computer is also included in each embodiment. That is, computer-readable storage media are also included in the scope of each embodiment. In addition, not only the storage medium on which the above-mentioned program is recorded but also the program itself is included in each embodiment. Also, one or more components included in the above embodiments may be circuits such as ASICs (Application Specific Integrated Circuits), FPGAs (Field Programmable Gate Arrays), etc., configured to implement the functions of each component.

As the storage medium, for example, a floppy disk, a hard disk, an optical disk, a magneto-optical disk, a CD (Compact Disk)-ROM, a magnetic tape, a nonvolatile memory card, and a ROM can be used. In addition, not only the programs recorded on the storage medium that execute processing by themselves, but also those that operate on the OS (Operating System) and execute processing in cooperation with other software and the functions of the expansion board are included in the scope of each embodiment.

The services implemented by the functions of the embodiments described above may also be provided to the user in the form of Software as a Service (SaaS).

It should be noted that the embodiments described above are merely examples of the embodiment of the disclosure, and the technical scope of the disclosure should not be construed as being limited thereto. That is, the disclosure can be practiced in a variety of ways without departing from its technical philosophy or its principal features.

Some or all of the above embodiments may also be described as follows, but are not limited to.

(Supplementary Note 1)

An information processing device comprising:
an acquisition unit configured to acquire acoustic characteristics in a frequency domain based on a sound wave propagating in a head of a user; and
an extracting unit configured to generate a first frequency response function having a rational polynomial equation to extract feature quantity used for biometric authentication of the user based on the first frequency response function, the rational polynomial equation including terms indicating feature of a peak of the acoustic characteristics in a denominator and terms indicating feature of a notch of the acoustic characteristics in a numerator.

(Supplementary Note 2)

The information processing device according to supplementary note 1, wherein the extracting unit is configured to extract coefficients of the rational polynomial equation as the feature quantity.

(Supplementary Note 3)

The information processing device according to supplementary note 1 or 2, wherein the denominator of the first frequency response function is zero at a frequency corresponding to the peak.

(Supplementary Note 4)

The information processing device according to any one of supplementary notes 1 to 3, wherein the acoustic characteristics include a plurality of peaks and wherein the extracting unit is configured to generate a second frequency response function having a sum of a plurality of fractions.

(Supplementary Note 5)

The information processing device according to supplementary note 4, wherein imaginary part in each denominator of the plurality of fractions is zero at a frequency corresponding to one of the plurality of peaks.

(Supplementary Note 6)

The information processing device according to supplementary note 4 or 5, wherein the first frequency response function and the second frequency response function are mutually convertible.

(Supplementary Note 7)

The information processing device according to supplementary note 6, wherein the second frequency response function includes a partial fractional expansion of the first frequency response function.

(Supplementary Note 8)

The information processing device according to any one of supplementary notes 4 to 7, wherein the extracting unit is configured to generate the first frequency response function by excluding some terms from the plurality of fractions included in the second frequency response function and converting to the first frequency response function.

(Supplementary Note 9)

The information processing device according to any one of supplementary notes 4 to 8, wherein the extracting unit is configured to generate the first frequency response function by excluding physically non-significant terms from the plurality of fractions included in the second frequency response function and converting to the first frequency response function.

(Supplementary Note 10)

The information processing device according to any one of supplementary notes 4 to 9, wherein the extracting unit is configured to generate the first frequency response function by excluding unstable terms for changing calculation conditions from the plurality of fractions included in the second frequency response function and converting to the first frequency response function.

(Supplementary Note 11)

The information processing device according to any one of supplementary notes 8 to 10, wherein the extracting unit is configured to generate spectrum in the frequency domain by using the first frequency response function converted from the second frequency response function.

(Supplementary Note 12)

The information processing device according to supplementary note 11, wherein the extracting unit is configured to extract the feature quantity based on the spectrum.

(Supplementary Note 13)

The information processing device according to supplementary note 11 or 12, wherein the extracting unit is configured to extract a first feature quantity based on coefficients of the first frequency response function and extract a second feature quantity based on the spectrum.

(Supplementary Note 14)

The information processing device according to any one of supplementary notes 1 to 13, wherein the acoustic characteristics depend on a sound wave propagated in an ear canal of the user, the sound wave being acquired by a wearable device worn on the head of the user.

(Supplementary Note 15)

An information processing method comprising:
acquiring acoustic characteristics in a frequency domain based on a sound wave propagating in a head of a user; and
generating a first frequency response function having a rational polynomial equation to extract feature quantity used for biometric authentication of the user based on the first frequency response function, the rational polynomial equation including terms indicating feature of a peak of the acoustic characteristics in a denominator and terms indicating feature of a notch of the acoustic characteristics in a numerator.

(Supplementary Note 16)

A storage medium storing a program that causes a computer to perform:

acquiring acoustic characteristics in a frequency domain based on a sound wave propagating in a head of a user; and generating a first frequency response function having a rational polynomial equation to extract feature quantity used for biometric authentication of the user based on the first frequency response function, the rational polynomial equation including terms indicating feature of a peak of the acoustic characteristics in a denominator and terms indicating feature of a notch of the acoustic characteristics in a numerator.

REFERENCE SIGNS LIST 1 information communication device
2 earphone
3 user
20 earphone control device
26 speaker
27 microphone
101, 201 CPU
102, 202 RAM
103, 203 ROM
104 HDD
105, 207 communication I/F
106 input device
107 output device
121 acoustic characteristic acquisition unit
122 feature quantity extraction unit
123 determination unit
204 flash memory
205 speaker I/F
206 microphone I/F
208 battery
421 acquiring unit
422 extraction unit

What is claimed is:

1. An information processing device comprising:
a memory configured to store instructions; and
a processor configured to execute the instructions to:
acquire acoustic characteristics in a frequency domain based on a sound wave propagating in a head of a user; and
generate a first frequency response function having a rational polynomial equation to extract feature quantity used for biometric authentication of the user based on the first frequency response function, the rational polynomial equation including terms indicating feature of a peak of the acoustic characteristics in a denominator and terms indicating feature of a notch of the acoustic characteristics in a numerator.

2. The information processing device according to claim 1, wherein coefficients of the rational polynomial equation is extracted as the feature quantity.

3. The information processing device according to claim 1, wherein the denominator of the first frequency response function is zero at a frequency corresponding to the peak.

4. The information processing device according to claim 1, wherein the acoustic characteristics include a plurality of peaks and wherein a second frequency response function having a sum of a plurality of fractions is generated.

5. The information processing device according to claim 4, wherein imaginary part in each denominator of the plurality of fractions is zero at a frequency corresponding to one of the plurality of peaks.

6. The information processing device according to claim 4, wherein the first frequency response function and the second frequency response function are mutually convertible.

7. The information processing device according to claim 6, wherein the second frequency response function includes a partial fractional expansion of the first frequency response function.

8. The information processing device according to claim 4, wherein the first frequency response function is generated by excluding some terms from the plurality of fractions included in the second frequency response function and converting to the first frequency response function.

9. The information processing device according to claim 4, wherein the first frequency response function is generated by excluding physically non-significant terms from the plurality of fractions included in the second frequency response function and converting to the first frequency response function.

10. The information processing device according to claim 4, wherein the first frequency response function is generated by excluding unstable terms for changing calculation conditions from the plurality of fractions included in the second frequency response function and converting to the first frequency response function.

11. The information processing device according to claim 8, wherein spectrum in the frequency domain is generated by using the first frequency response function converted from the second frequency response function.

12. The information processing device according to claim 11, wherein the feature quantity is extracted based on the spectrum.

13. The information processing device according to claim 11, wherein a first feature quantity is extracted based on coefficients of the first frequency response function and a second feature quantity is extracted based on the spectrum.

14. The information processing device according to claim 1, wherein the acoustic characteristics depend on a sound wave propagated in an ear canal of the user, the sound wave being acquired by a wearable device worn on the head of the user.

15. An information processing method comprising:
acquiring acoustic characteristics in a frequency domain based on a sound wave propagating in a head of a user; and
generating a first frequency response function having a rational polynomial equation to extract feature quantity used for biometric authentication of the user based on the first frequency response function, the rational polynomial equation including terms indicating feature of a peak of the acoustic characteristics in a denominator and terms indicating feature of a notch of the acoustic characteristics in a numerator.

16. A non-transitory storage medium storing a program that causes a computer to perform:
acquiring acoustic characteristics in a frequency domain based on a sound wave propagating in a head of a user; and
generating a first frequency response function having a rational polynomial equation to extract feature quantity used for biometric authentication of the user based on the first frequency response function, the rational polynomial equation including terms indicating feature of a peak of the acoustic characteristics in a denominator and terms indicating feature of a notch of the acoustic characteristics in a numerator.

\* \* \* \* \*